(12) United States Patent
Huang

(10) Patent No.: US 7,779,696 B2
(45) Date of Patent: Aug. 24, 2010

(54) SEPARATE CMUTS FOR RECEPTION AND TRANSMISSION

(75) Inventor: Yongli Huang, San Jose, CA (US)

(73) Assignee: Kolo Technologies, Inc., San Jose, CA (US)

( * ) Notice: Subject to any disclaimer, the term of this patent is extended or adjusted under 35 U.S.C. 154(b) by 508 days.

(21) Appl. No.: 11/696,664

(22) Filed: Apr. 4, 2007

(65) Prior Publication Data

US 2007/0287918 A1    Dec. 13, 2007

Related U.S. Application Data

(60) Provisional application No. 60/744,242, filed on Apr. 4, 2006.

(51) Int. Cl.
*G01N 29/32* (2006.01)
*A61B 8/14* (2006.01)

(52) U.S. Cl. .................... 73/626; 73/632; 600/437; 600/459; 367/181; 367/170

(58) Field of Classification Search ............ 73/626, 73/632; 600/437, 459; 367/181, 170
See application file for complete search history.

(56) References Cited

U.S. PATENT DOCUMENTS 6,605,043 B1 * 8/2003 Dreschel et al. ............. 600/459
2003/0028109 A1 * 2/2003 Miller .......................... 600/437
2005/0094490 A1 * 5/2005 Thomenius et al. .......... 367/155
2005/0154300 A1 * 7/2005 Wodnicki et al. ............ 600/437
2005/0219953 A1 * 10/2005 Bayram et al. ............... 367/178
2006/0173342 A1 * 8/2006 Panda et al. .................. 600/459
2007/0228877 A1 * 10/2007 Huang ......................... 310/322
2008/0197751 A1 * 8/2008 Huang ......................... 310/311
2009/0048522 A1 * 2/2009 Huang ......................... 600/459

* cited by examiner

*Primary Examiner*—Hezron Williams
*Assistant Examiner*—Rose M Miller
(74) *Attorney, Agent, or Firm*—Lee & Hayes, PLLC

(57) ABSTRACT

A capacitive micromachined ultrasonic transducers (cMUT) system has two cMUTs connected to each other. The first cMUT is adapted for operation in a transmission mode, and the second cMUT is adapted for operation in the reception mode. The first cMUT and the second cMUT share a common signal line and are connected in a manner to allow the first cMUT and the second cMUT to have bias voltages that can be independently set. In one embodiment, one of the cMUTs is connected to a voltage controller to regulator the voltage applied there on. Various connection configurations, including connections in series and connections in parallel, are disclosed. The cMUT system configurations allow separate optimization for transmission and reception and better flexibility in operation.

18 Claims, 7 Drawing Sheets

SEPARATE CMUTS FOR RECEPTION AND TRANSMISSION

PRIORITY

This application claims priority from U.S. Provisional Applications Ser. No. 60/744,242, filed Apr. 4, 2006.

BACKGROUND

The present invention relates capacitive micromachined ultrasonic transducers (cMUT), particularly to methods for operating cMUT.

Capacitive micromachined ultrasonic transducers (cMUTs) are electrostatic actuator/transducers, which are widely used in various applications. Ultrasonic transducers can operate in a variety of media including liquids, solids and gas. These transducers are commonly used for medical imaging for diagnostics and therapy, biochemical imaging, non-destructive evaluation of materials, sonar, communication, proximity sensors, gas flow measurements, in-situ process monitoring, acoustic microscopy, underwater sensing and imaging, and many others. In addition to discrete ultrasound transducers, ultrasound transducer arrays containing multiple transducers have been also developed. For example, two-dimensional arrays of ultrasound transducers are developed for imaging applications.

Compared to the widely used piezoelectric (PZT) ultrasound transducer, the MUT has advantages in device fabrication method, bandwidth and operation temperature. For example, making arrays of conventional PZT transducers involves dicing and connecting individual piezoelectric elements. This process is fraught with difficulties and high expenses, not to mention the large input impedance mismatch problem presented by such elements to transmit/receiving electronics. In comparison, the micromachining techniques used in fabricating MUTs are much more capable in making such arrays. In terms of performance, the MUT demonstrates a dynamic performance comparable to that of PZT transducers. For these reasons, the MUT is becoming an attractive alternative to the piezoelectric (PZT) ultrasound transducers.

The basic structure of a cMUT is a parallel plate capacitor with a rigid bottom electrode and a top electrode residing on or within a flexible membrane, which is used to transmit (TX) or detect (RX) an acoustic wave in an adjacent medium. A DC bias voltage is applied between the electrodes to deflect the membrane to an optimum position for cMUT operation, usually with the goal of maximizing sensitivity and bandwidth. During transmission an AC signal is applied to the transducer. The alternating electrostatic force between the top electrode and the bottom electrode actuates the membrane in order to deliver acoustic energy into the medium surrounding the cMUT. During reception the impinging acoustic wave vibrates the membrane, thus altering the capacitance between the two electrodes. An electronic circuit detects this capacitance change.

Two representative types of cMUT structures are conventional flexible membrane cMUT and the newer embedded-spring cMUT (ESCMUT). FIG. 1 shows a schematic cross-sectional view of a conventional flexible membrane cMUT 10, which has a fixed substrate 101 having a bottom electrode 120, a flexible membrane 110 connected to the substrate 101 through membrane supports 130, and a movable top electrode 150. The flexible membrane 110 is spaced from the bottom electrode 120 by the membrane supports 130 to form a transducing space 160.

FIG. 2 is a schematic cross-sectional view of embedded-spring cMUT (ESCMUT) 200, which is described in the PCT International Application No. PCT/IB2006/051568, entitled MICRO-ELECTRO-MECHANICAL TRANSDUCERS, filed on May 18, 2006; and International Application (PCT) No. PCT/IB2006/051569, entitled MICRO-ELECTRO-MECHANICAL TRANSDUCERS, filed on May 18, 2006, particularly the cMUTs shown in FIGS. 5A-5D therein. The cMUT 200 has a substrate 201, on top of which is a spring anchor 203 supporting a spring layer 210; a surface plate 240 connected to the spring layer 210 through spring-plate connectors 230; and a top electrode 250 connected to the surface plate 240. The cMUT 200 may be only a portion of a complete cMUT element (not shown).

Although structurally and mechanically very different, cMUTs 100 and 200 in FIGS. 1-2, and most other cMUTs, can be commonly represented by a simplified schematic model. FIG. 3A shows a simplified schematic cMUT model 300 which shows capacitor 310 consisting of fixed electrode 310a and movable electrode 310b, which is connected to equivalent springs 320 anchored by spring anchors 330. The fixed electrode 310a and the mobile electrode 310b define transducing space 360 therebetween. The electrodes 310a and 310b are connected to an interface circuit 380. The cMUT model can be further simplified as a circuit model having a variable capacitor as shown in FIG. 3B. The variable capacitor 310 in FIG. 3B has two electrodes 310a and 310b and is connected to the interface circuit 380.

Essentially all cMUTs based on a variable capacitor, even comb driver cMUTs in which the movable electrode is laterally displaced (along the direction of the electrode surface), may be represented by the variable capacitor model 300 shown in FIG. 3B. In this description, the variable capacitor model 300 shown in FIG. 3B is be used to represent any cMUT regardless of its structural and mechanical characteristics.

Usually a cMUT is biased with a DC voltage either directly or through a bias circuit. The cMUT also connects to an interface circuit, which usually comprises a switch, a transmission (TX) port and a reception (RX) port. In transmission, a transmission input signal is applied on the cMUT through the transmission port to move a movable electrode of the cMUT, which in turn energizes the medium and transmit acoustics energy into the medium. In reception, acoustic energy impinging on the cMUT is detected electrically by an interface circuit through the reception port. The switch switches the connection of the cMUT to either transmission port or reception port during operation.

Much effort has been made to improve the cMUT performance by designing new cMUT structures that may have better bandwidth, higher sensitivity, and more compact size, and are easier and cheaper to fabricate. However, given the cMUT structure, there is also room to improve the performance of a cMUT system using improved operation methods and cMUT system configurations.

SUMMARY OF THE DISCLOSURE

This application discloses operation methods and connection configurations using separated cMUTs used for reception (RX) and transmission (TX) operations. Two cMUTs are connected to each other, with one adapted for transmission and the other for reception. The two cMUT share a common signal line (or cable), yet provide independent electrical controls on each cMUT.

Several exemplary configurations for connecting two cMUTs separately used for RX and TX are disclosed. One exemplary embodiment is to connect two cMUTs in series and another exemplary embodiment is to connect two cMUTs in parallel.

In some embodiments, an electrode of the cMUT for transmission and an electrode of the cMUT for reception are directly connected to each other to share a common bias level, but least one electrode of the two cMUTs is connected to an independently set bias level to allow the two cMUTs to have different bias voltages. In one embodiment, the cMUT for transmission has a zero bias voltage across its two electrodes, while the cMUT for reception has a nonzero bias voltage across its two electrodes.

A voltage controller may be used to regulate the amount of transmission input signal which passes through the cMUT for reception. DC decouplers are also used to improve performance.

DETAILED DESCRIPTION

Figure 1:
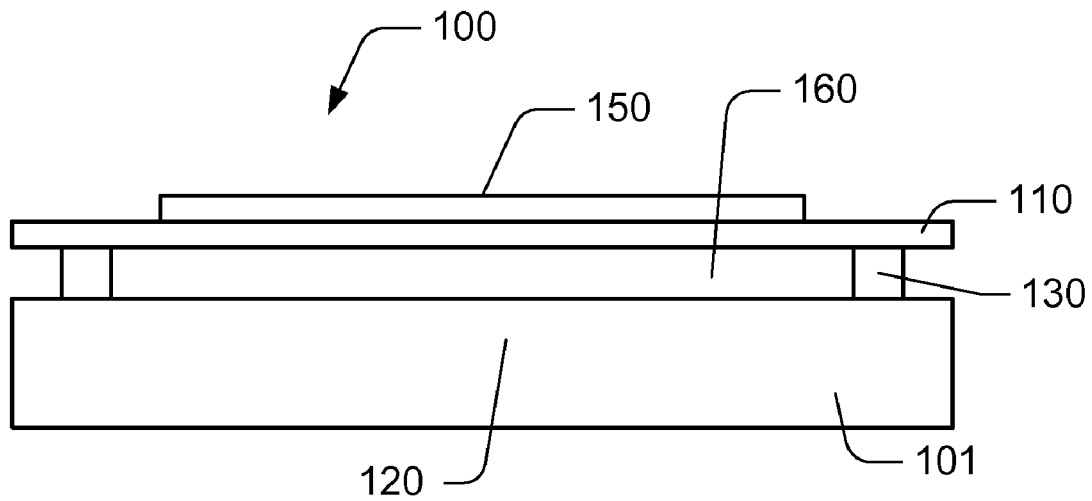
FIG. 1 is a schematic cross-sectional view of a conventional flexible membrane cMUT.
Figure 2:
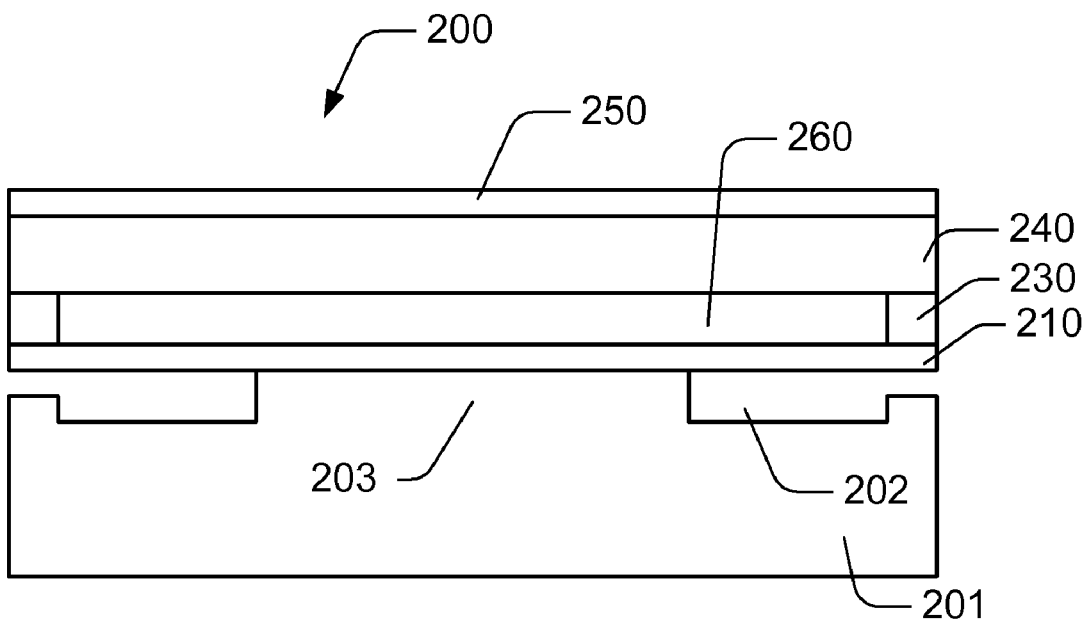
FIG. 2 is a schematic cross-sectional view of embedded-spring cMUT (ESCMUT).
Figure 3A:
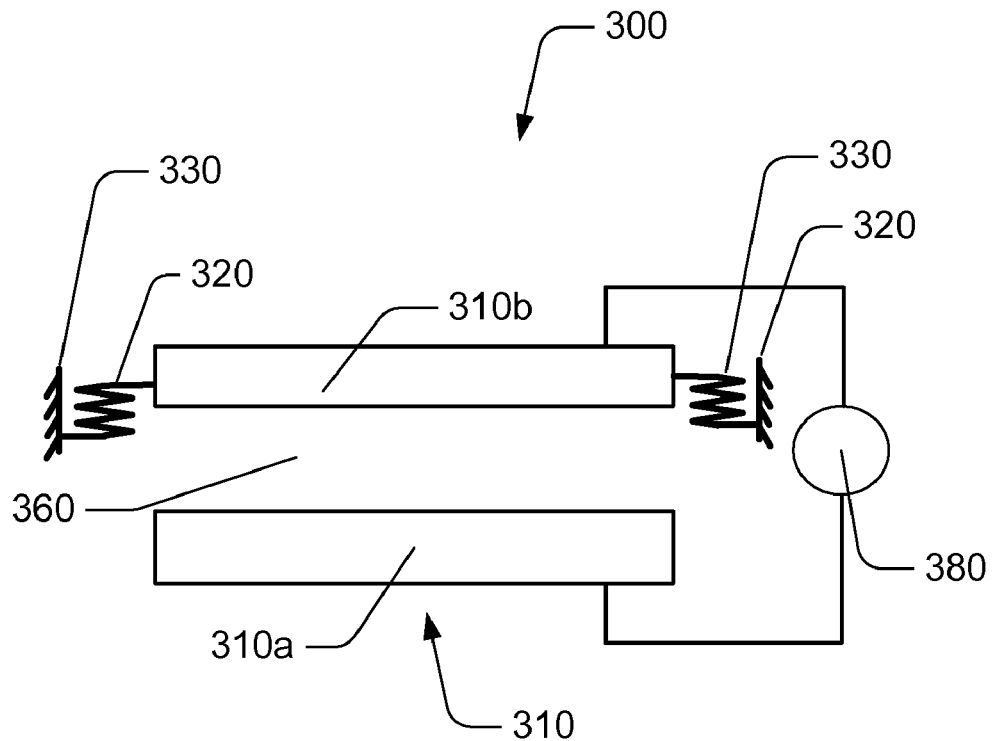
FIG. 3A shows a simplified schematic cMUT model
Figure 3B:
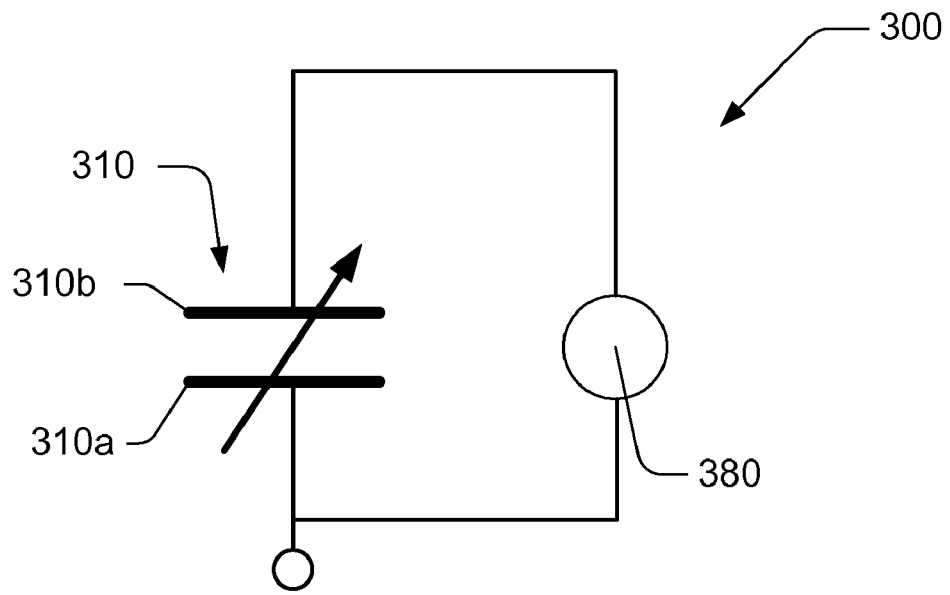
FIG. 3B shows a further simplified circuit model having a variable capacitor representing a cMUT.

The capacitive micromachined ultrasonic transducer (cMUT) system having separate cMUT for transmission and reception are described in detail along with the figures, in which like parts are denoted with like reference numerals or letters. The methods are adapted for transmitting an ultrasonic signal and/or receiving a pressure signal using a cMUT system.

The cMUT system and its operation method address a design trade-off that exist in the current cMUT systems and operating methods which usually use the same cMUT for both reception (RX) and transmission (TX) operations. Because of a large displacement difference in reception and transmission operations of a cMUT, trade-offs to balance the transmission performance and the reception performance are usually necessary in these existing systems and methods, thus greatly limiting the overall performance of a cMUT system.

The cMUT system and the operation method disclosed herein use separated cMUTs for transmission and reception operations. This configuration allows cMUTs to be optimized for transmission and reception separately with minimum trade-off and used in the same system.

Since the cMUT system uses two cMUTs to replace a single cMUT, the method to connect or configure the cMUTs for separated RX and TX is different from that of a single cMUT used for both RX and TX. In the following, various cMUT configurations, including both simple separate-line designs and more sophisticated designs, are described.

Figure 4:
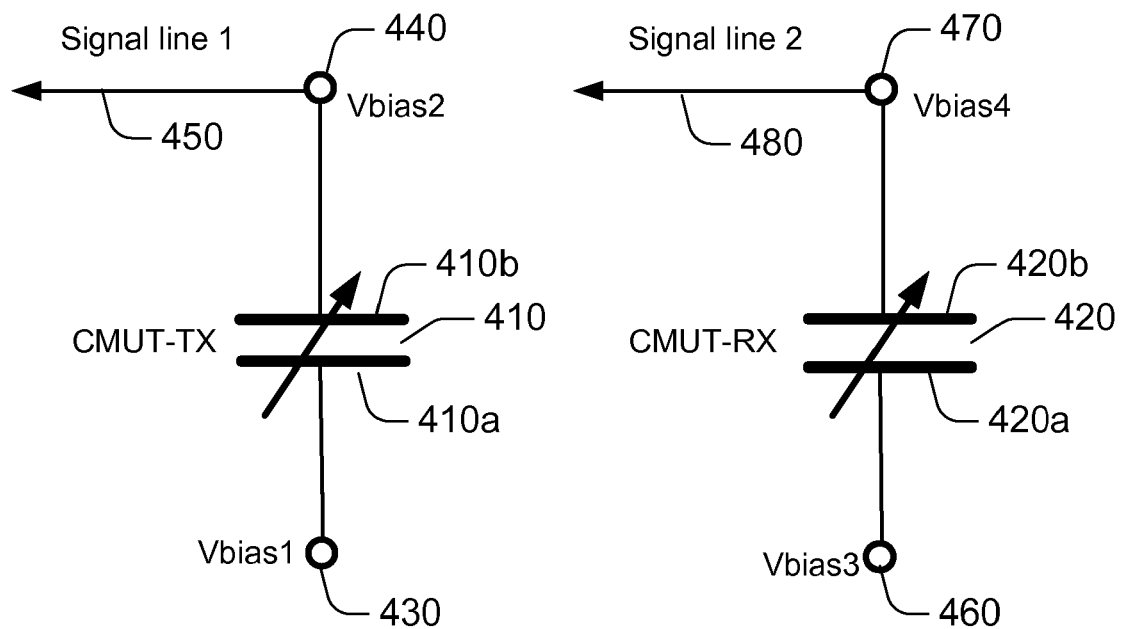
FIG. 4 shows a simple dual cMUT system using separate signal lines for each cMUT.

FIG. 4 shows a simple dual cMUT system using separate signal lines for each cMUT. The cMUT system has cMUT 410 for transmission and cMUT 420 for reception. In this configuration, cMUTs 410 and 420 have different bias. The cMUT 410 has bias 430 applied on electrode 410a and bias 440 applied on electrode 410b, and is connected to signal line 450. The cMUT 420 has bias 460 on electrode 420a and bias 470 on electrode 420b, and is connected to signal line 480. The transmission signal (not shown) is only applied on the cMUT 410. One disadvantage with this approach is that the number of the signal lines (or cables) to connect the transducers in the system is doubled. This may be undesirable if an array with larger number of transducer elements is used.

Figure 5:
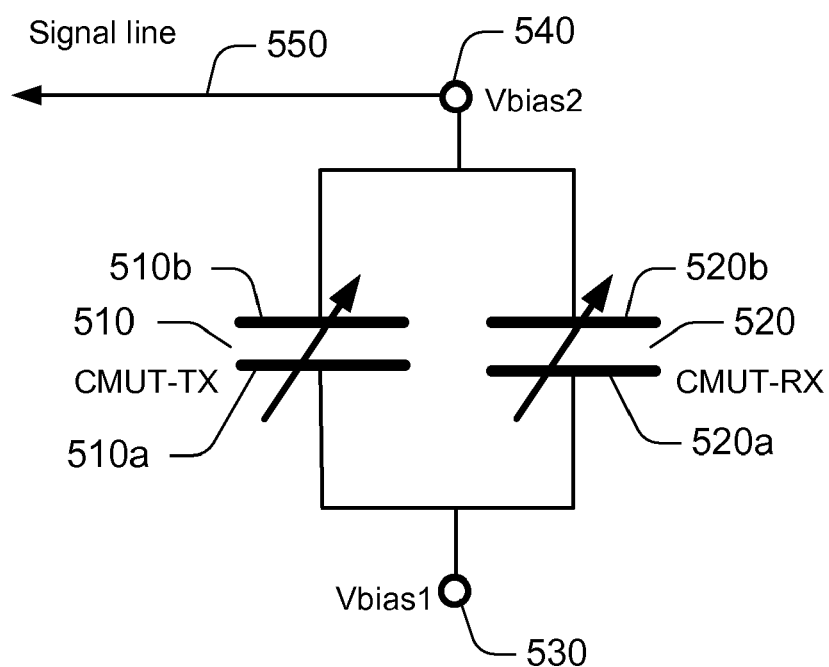
FIG. 5 shows a dual cMUT system arranged in parallel sharing a common signal line.

FIG. 5 shows a dual cMUT system arranged in parallel sharing a common signal line. In this configuration, cMUT 510 is used for transmission and cMUT 520 is used for reception. The cMUT 510 and the cMUT 520 are connected in parallel with each other sharing of bias 530 at one side (electrode 510a and 520a) and bias 540 at the other side (electrode 510b and 520b). The cMUT 510 and the cMUT 520 also share the same signal line 550. This configuration is more economical on wiring and cable, but because both cMUTs 510 and 520 share the same DC biases (530 and 540), the flexibility to operate the cMUTs 510 and 520 independently may suffer. Even though both cMUTs 510 and 520 themselves may be optimized for transmission and reception respectively, they may not be operated optimally. Moreover, the larger transmission signal may be undesirable for the cMUT 520 that is optimized for reception.

In order to take more advantages of the separation of cMUTS for transmission and reception operation, more sophisticated configurations and operation methods are described below that allow cMUTs to be not only separately optimized for transmission and reception operations, but also operated relatively independently.

There are two basic types of connection configurations to connect two cMUTs that are used for transmission and reception separately but share the same signal line (or cable). One type is to connect the two cMUTs in series, and the other is to connect two cMUTs in parallel. In a practical implementation of these connection configurations, it is usually preferred that no electrode of the cMUTs is left floating. Therefore, the cMUT electrodes should preferably be either connected to a signal source or the input of a front-end circuit, or set to a desired bias voltage level (Vbias). The bias voltage level (Vbias) includes any DC voltage level and electrical ground (GND).

Figure 6:
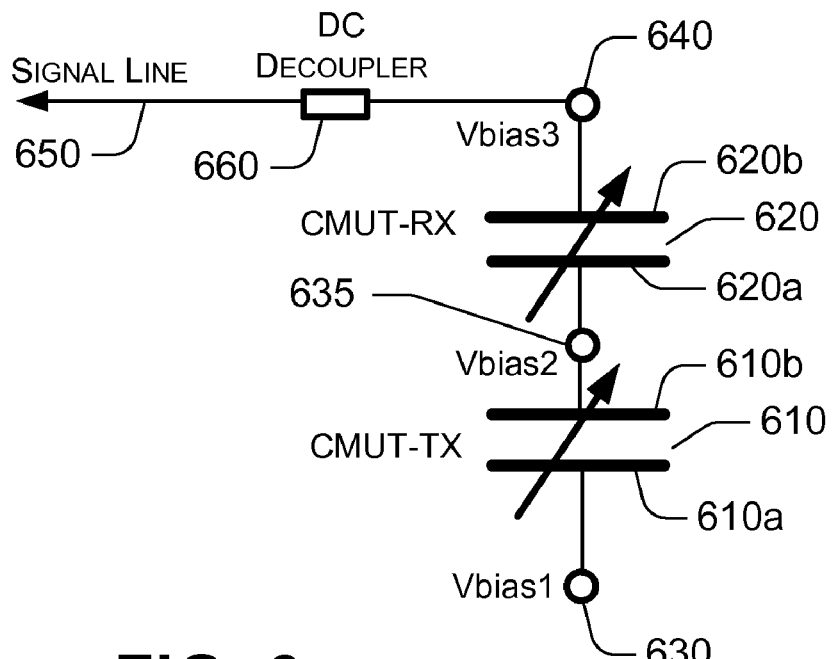
FIG. 6 shows a basic configuration to connect two cMUTs performing transmission and reception separately in series.

FIG. 6 shows a basic configuration to connect two cMUTs performing transmission and reception separately in series. Two cMUT 610 and 620 are connected in series and the position of two cMUTs 610 and 620 may be switched. In this configuration, cMUT 610 is adapted for operation in transmission mode and cMUT 620 is adapted for operation in reception mode. The two cMUTs 610 and 620 share a common signal line 650, which may be used for transporting both the transmission input signal (not shown) and the output signal.

The electrode 610*b* of cMUT 610 and the electrode 620*a* of the cMUT 620 are directly connected to each other, sharing the same bias level Vbias2. In practice, the electrode 610*b* and the electrode 620*a* may be the same common electrode shared by the two cMUTs 610 and 620, especially if both the electrode 610*b* and 620*a* are static electrodes anchored on a substrate. The electrodes 610*b* and 620*a* (or the common electrode 610*b*/620*a*) may be set at a bias level Vbias2 through a bias setter 635. The electrodes (610*a* and 620*b*) of two cMUTs may be set to desired bias levels, Vbias1 and Vbias3, respectively, through bias setters 630 and 640. The independence of Vbias1 and Vbias3 afford operation flexibility to the cMUT system. Specifically, because the bias voltage across the cMUT 610 is Vbias1−Vbia2, and the bias voltage across the cMUT 620 is Vbias3−Vbias2, the bias voltages of the two cMUT 610 and 620 may be set independently as the bias levels Vbias1 and Vbias3 can be set independently. Two cMUTs 610 and 620 may have the same or different DC bias voltage across the two electrodes, depending on the operation requirements. In some embodiments, the cMUT 610 for transmission is not biased. That is, no net bias voltage is applied across the two electrodes 610*a* and 610*b* in operation. This may be accomplished by setting Vbias2=Vbias1. For example, both Vbias2 and Vbias1 may be set to zero.

A DC de-coupler device 660, e.g. a capacitor, may be placed between the signal line 650 and the cMUT 610. Depending on the bias setting, The DC de-coupler device 660 may be optional. This configuration is economical on its use of wiring or cable, but allows more flexibility of operating the cMUT system.

It is appreciated that not all three bias levels Vbias1, Vbias2, and Vbias3 are required. For example, the cMUT configuration of FIG. 6 may do without the bias setter 640 for setting Vbias3 and still has enough flexibility for individual bias settings for the two cMUTs 610 and 620. To do without bias setter 640, the electrode 620*b* may be directly connected to the DC decoupler 660 without having the bias setter 640.

In the above configuration, the cMUT 610 is adapted for operation in the transmission mode, while the cMUT 620 is adapted for operation in the reception mode. Because the cMUT 610 does not need to operate in the reception mode, it may be optimized for operation in the transition mode. Likewise, because the cMUT 620 does not need to operate in the transmission mode, it may be optimized for operation in the reception mode. The optimization may take into consideration of the characteristics of reception mode and transmission mode, such as maximum displacement of the movable electrodes in each mode, the differences of medium interface in each mode, and whether the emphasis is on the sensitivity or low distortion of the signal. In addition, separate cMUTs can be designed to have different frequency response for transmission and reception operation.

Figure 7:
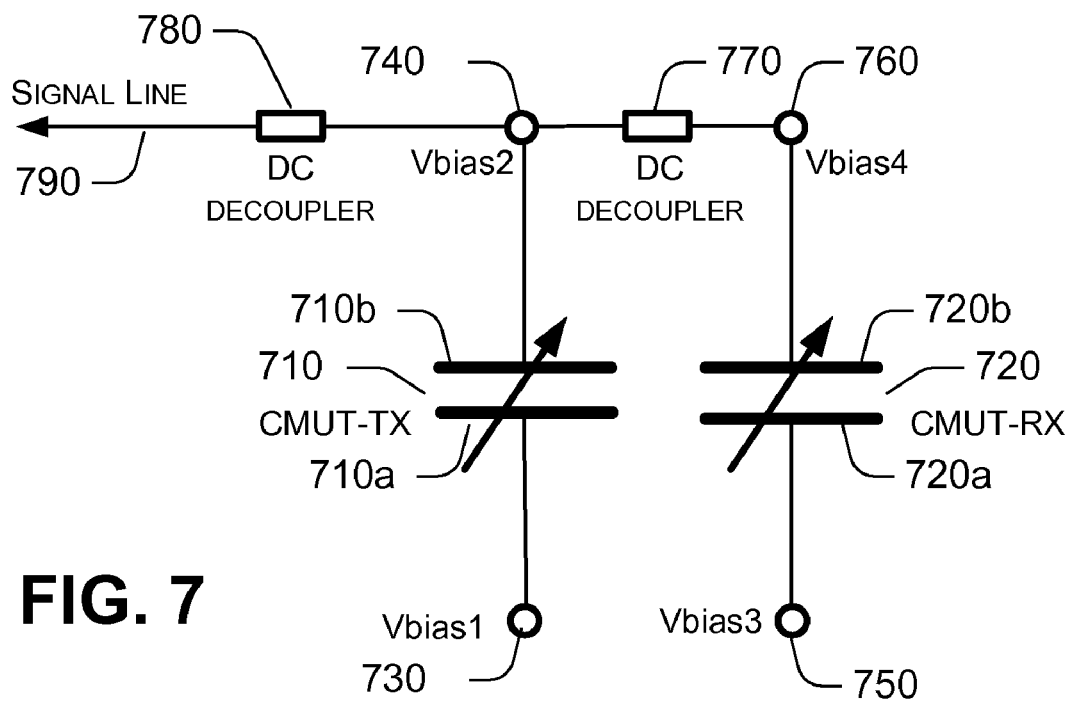
FIG. 7 shows a basic configuration to connect two cMUTs performing reception and transmission separately in parallel.

FIG. 7 shows a basic configuration to connect two cMUTs performing reception and transmission separately in parallel. Two cMUT 710 and 720 are connected in parallel to each other and the position of two cMUTs 710 and 720 may be switched. Like that in the cMUT system of FIG. 6, cMUT 710 is adapted for operation in transmission mode and cMUT 720 is adapted for operation in reception mode. The two cMUTs 710 and 720 share a common signal line 750, which may be used for transporting both the transmission input signal (not shown) and the output signal.

In this configuration, the two electrodes 710*a* and 710*b* of cMUT 710 for transmission may be set to bias levels Vias1 and Vbias2, respectively, through bias setters 730 and 740; and the two electrodes 720*a* and 720*b* of cMUT 720 for reception may be set to bias levels Vias3 and Vbias4, respectively, through bias setters 750 and 760. A DC decoupler 770 (e.g., a capacitor) is placed between two electrodes 710*b* and 720*b* of two cMUTs 710 and 720 so that the two electrodes 710*b* and 720*b* may be set to different bias levels Vbias2 and Vbias4. The DC decoupler 770 is optional if Vbias1 and Vbias3 are already different and therefore further difference between Vbias2 and Vbias4 may be unnecessary. In addition, a DC decoupler 780 (e.g., a capacitor) may be placed between the signal line 790 and the cMUTs 710 and 720. Depending on the bias setting, the DC decoupler 780 may be optional. Like the configuration of FIG. 6, the cMUT configuration of FIG. 7 offers operation flexibility in terms of individually selectable bias levels for the two cMUT 710 and 720.

In the cMUT configurations of FIG. 6 and FIG. 7, although two cMUTs may be biased differently, the transmission signal when applied on the transmission cMUT (610 and some 10) will also be partially applied on the cMUT for reception. The fraction of the transmission signal applied on the reception cMUT may be adjusted by the capacitance ratio between two cMUTs (as in FIG. 6) or the impedance ratio between the DC decoupler 770 and the cMUT 710 for reception (as in FIG. 7). Since the cMUT reception operation needs a bias only and not an input signal, a voltage controller may be introduced into the configurations in FIG. 6 and FIG. 7 to further remove the effect of the transmission signal on the cMUT for reception.

Figure 8:
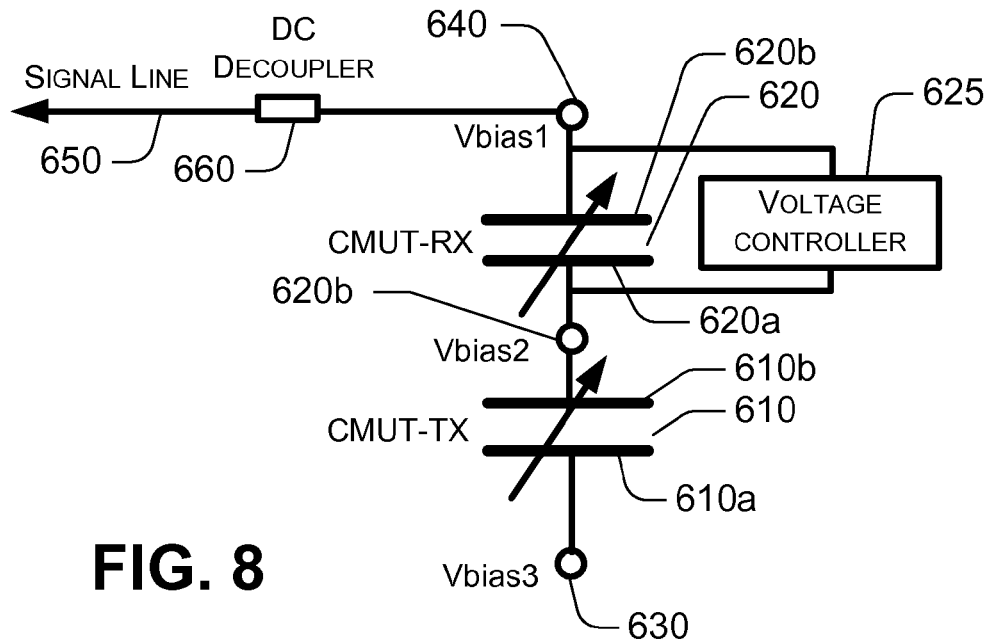
FIG. 8 shows a modification to the cMUT configuration of FIG. 6.

FIG. 8 shows a modification to the cMUT configuration of FIG. 6. This configuration is mostly the same as the configuration of FIG. 6 except for adding a voltage controller 625, which is connected to the cMUT 620 for reception. The voltage controller 625 regulates the voltage applied on the cMUT 620 for reception and the amount of the transmission signal that passes through the cMUT 620. The voltage controller 625 may be made of two diodes (or two series of multiple diodes) connected in parallel in opposite directions.

Like in FIG. 6, not all three bias levels Vbias 1, Vbias2, and Vbias3 are required. For example, the cMUT configuration of FIG. 8 may do without the bias setter 640 for setting Vbias1 and still has enough flexibility for individual bias settings for the two cMUTs 610 and 620. To do without the bias setter 640, the electrode 620*b* may be directly connected to the signal line 650 without having the DC decoupler 660.

Figure 9:
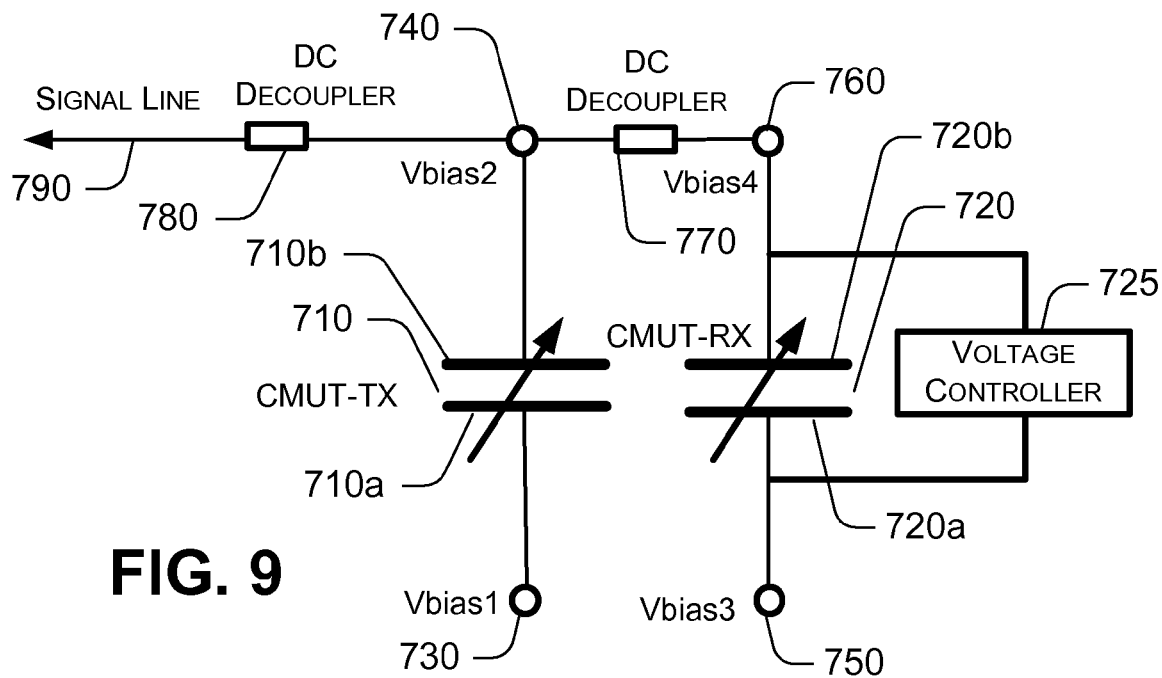
FIG. 9 shows a modification to the cMUT configuration of FIG. 7.

FIG. 9 shows a modification to the cMUT configuration of FIG. 7. This configuration is mostly the same as the configuration of FIG. 7 except for adding a voltage controller 725, which is connected to the cMUT 720 for reception. The voltage controller 725 regulates the voltage applied on the cMUT 720 for reception and the amount of the transmission signal that passes through the cMUT 720.

There are a variety of different ways to set a bias level in a cMUT connect configuration. One method is to connect a bias source (any DC voltage source or electrical ground) to a bias point (Vbias) through a resistor (R). Another method is to connect the bias source to a bias point (Vbias) through a switch. An AC signal may also be applied at the bias point (Vbias). If the AC signal is not desired at the bias point, the bias source may be directly connected to the bias point.

Figure 10:
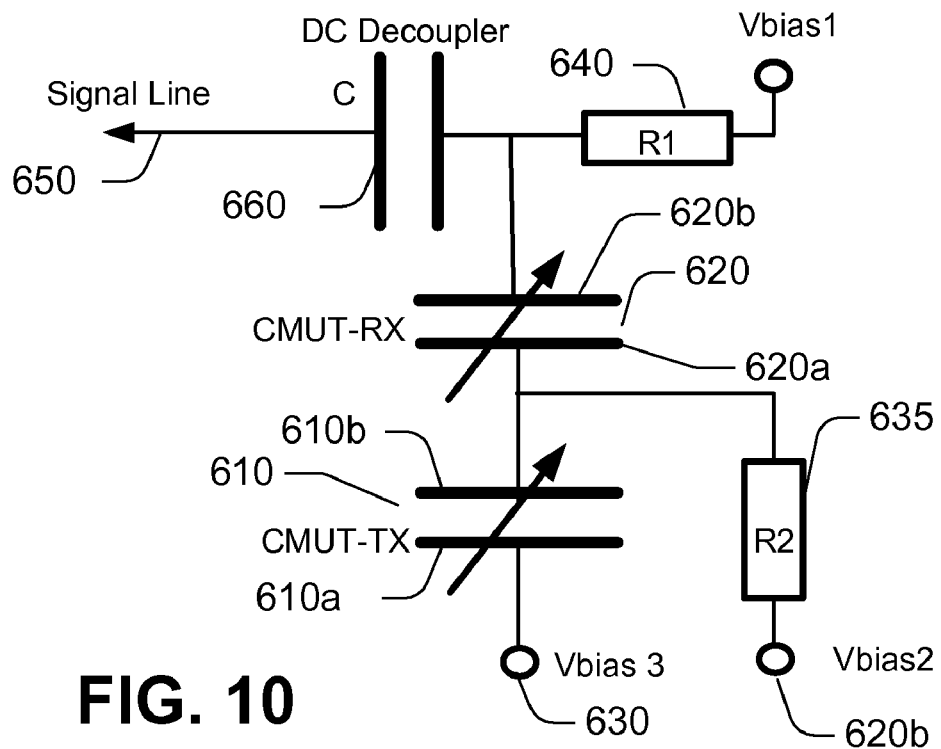
FIG. 10 shows the cMUT configuration of FIG. 6 with exemplary implementations of the DC decoupler and bias setters.

FIG. 10 shows the cMUT configuration of FIG. 6 with exemplary implementations of the DC decoupler and bias setters. The cMUT configuration of FIG. 10 is the same as that shown in FIG. 6, except that the decoupler 660 is shown to be implemented using a capacitor C, the bias setter 640 is implemented using a resistor R1, the bias setter 635 is implemented using a resistor R2, while the bias setter 630 is implemented using a direct connection.

Figure 11:
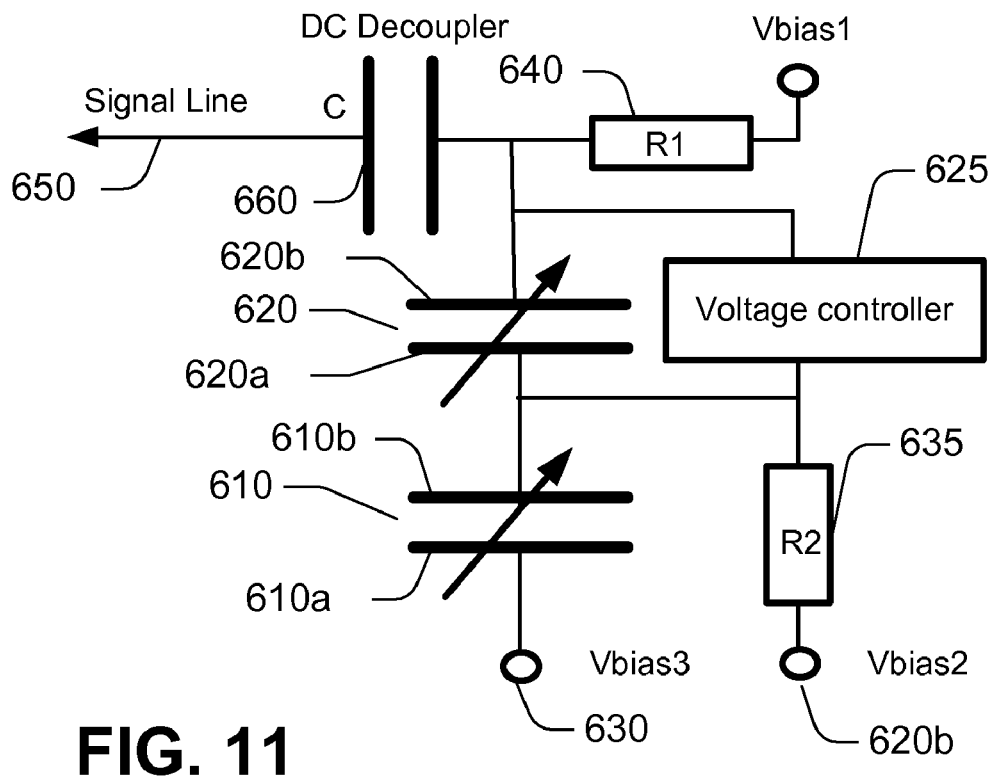
FIG. 11 shows the cMUT configuration of FIG. 8 with exemplary implementations of the DC decoupler and bias setters.

FIG. 11 shows the cMUT configuration of FIG. 8 with exemplary implementations of the DC decoupler and bias setters. The cMUT configuration of FIG. 11 is the same as that shown in FIG. 8, except that the decoupling 660 is shown to be implemented using capacitor C, the bias setter 640 is implemented using resistor R1, the bias setter 635 is implemented using resistor R2, while the bias setter 630 is implemented using a direct connection.

Figure 12:
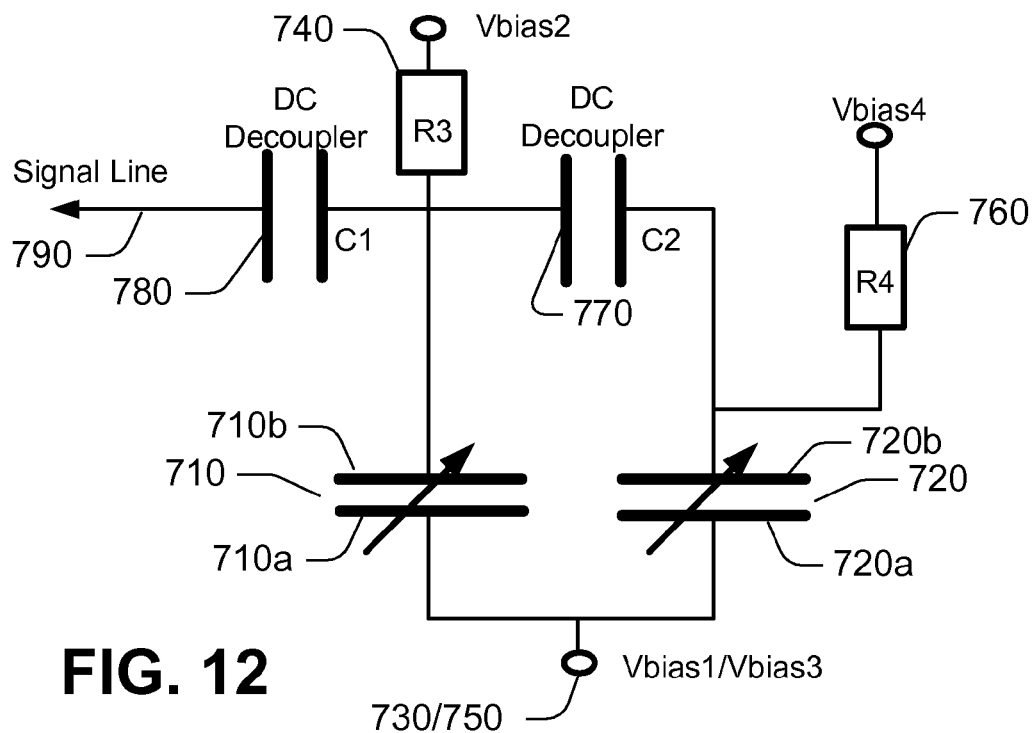
FIG. 12 shows the cMUT configuration of FIG. 7 with exemplary implementations of the DC decoupler and bias setters.

FIG. 12 shows the cMUT configuration of FIG. 7 with exemplary implementations of the DC decoupler and bias setters. The cMUT configuration of FIG. 12 is similar to that shown in FIG. 7, except that the decouplers 770 and 780 are shown to be implemented using capacitors C1 and C2, the bias setter 740 is implemented using a resistor R3, the bias setter 760 is implemented using a resistor R4, while the bias setters 730 and 750 are implemented using a direct connection. In addition, the two bias levels Vbias1 and Vbias3 are tied together to form one bias level, and therefore the electrode 710a of the cMUT 710 and the electrode 720a of the cMUT 720 share a common bias level. As shown, not all bias levels Vbias1, Vbias2, Vbias3 and Vbias4 and their associated bias setters 730, 740, 750 and 760 are required. Some may be eliminated or combined, as long as the overall bias voltage of the transmission cMUT 710 and the reception cMUT 720 chance to be set independently.

Figure 13:
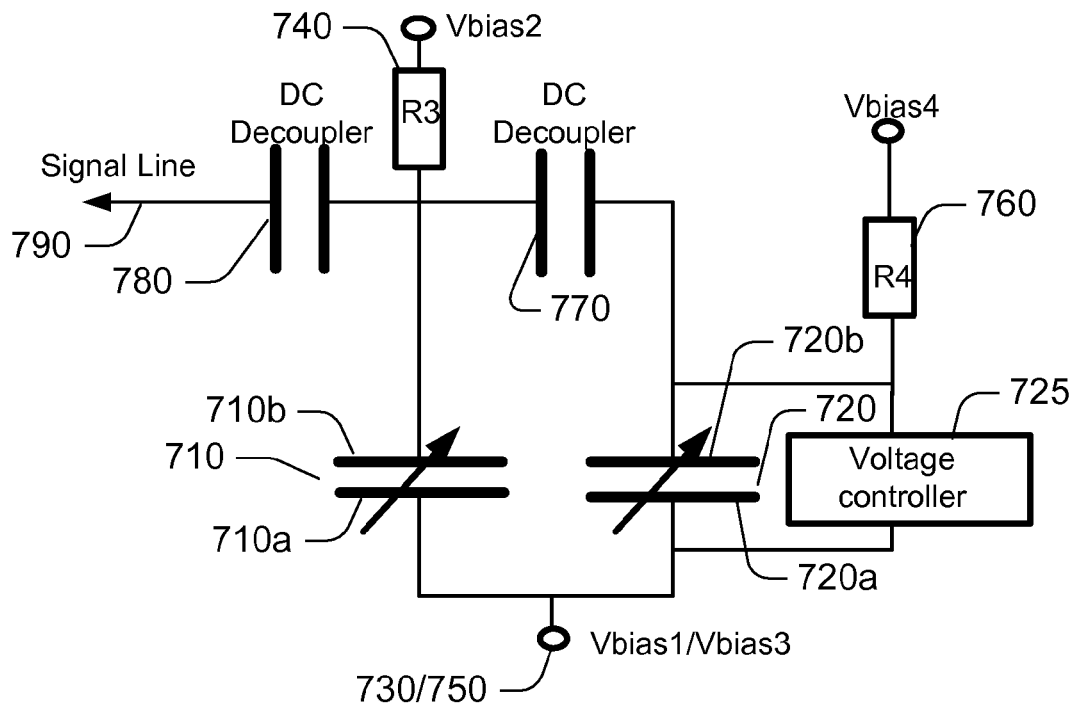
FIG. 13 shows the cMUT configuration of FIG. 9 with exemplary implementations of the DC decoupler and bias setters.

FIG. 13 shows the cMUT configuration of FIG. 9 with exemplary implementations of the DC decoupler and bias setters. The cMUT configuration of FIG. 13 is similar to that shown in FIG. 12 except that voltage controller 725 is added to regulate the voltage on the cMUT 720 for reception and the amount of the transmission signal that passes through the cMUT 720.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A capacitive micromachined ultrasonic transducer (cMUT) system comprising:
    a first cMUT having a first electrode and a second electrode, the first cMUT being adapted for operation in a transmission mode;
    a second cMUT having a third electrode and a fourth electrode, the second cMUT being adapted for operation in the reception mode, wherein the first cMUT and the second cMUT are connected to each other to share a common signal line to allow the first cMUT and the second cMUT to have different bias voltages in operation; and
    a voltage controller connected in parallel with the second cMUT to regulate an amount of transmission signal that passes through the second cMUT.

2. The cMUT system as recited in claim 1, wherein the first cMUT and the second cMUT are connected in series.

3. The cMUT system as recited in claim 1, wherein the first cMUT and the second cMUT are connected in parallel to each other.

4. The cMUT system as recited in claim 1, wherein the second electrode of the first cMUT and the third electrode of the second cMUT are directly connected to share a common bias level.

5. The cMUT system as recited in claim 1, wherein the first cMUT has a zero bias voltage across the first electrode and the second electrode in operation.

6. The cMUT system as recited in claim 1, wherein the first cMUT and the second cMUT are connected in series, and further comprising a capacitor as a DC decoupler connected between the second cMUT and the signal line.

7. The cMUT system as recited in claim 1, wherein the voltage controller is further connected to a bias setter.

8. The cMUT system as recited in claim 1, further comprising a DC coupler in the common signal line.

9. The cMUT system as recited in claim 1, wherein at least one of the first electrode, the second electrode, the third electrode, and the fourth electrode is connected to a bias setter.

10. The cMUT system as recited in claim 9, wherein the bias setter comprises a resistor.

11. The cMUT system as recited in claim 1, wherein the first electrode and the third electrode are connected to a first bias setter, the second electrode is connected to a second bias setter different from the first bias setter, and the fourth electrode is connected to a third bias setter, different from the first and second bias setters.

12. The cMUT system as recited in claim 1, wherein the first cMUT and the second cMUT are connected in series, and the second electrode and the third electrode are a single common electrode shared by the first cMUT and the second cMUT.

13. The cMUT system as recited in claim 1, wherein the first cMUT and the second cMUT are connected in parallel to each other, and the first electrode and the third electrode share a common bias level.

14. A capacitive micromachined ultrasonic transducer (cMUT) system comprising:
    a first cMUT having a first electrode and a second electrode, the first cMUT being adapted for operation in a transmission mode; and
    a second cMUT having a third electrode and a fourth electrode, the second cMUT being adapted for operation in the reception mode,
    wherein the first cMUT and the second cMUT are connected to each other to share a common signal line to allow the first cMUT and the second cMUT to have different bias voltages in operation,
    wherein the first electrode is connected to a first bias setter, the second electrode and the third electrode are connected to a second bias setter, different from the first bias setter, and the fourth electrode is connected to a third bias setter, different from the first and second bias setters.

15. The cMUT system as recited in claim 14, wherein the first cMUT and the second cMUT are connected in series, and the second electrode and the third electrode are a single common electrode shared by the first cMUT and the second cMUT.

16. The cMUT system as recited in claim 14, further comprising a voltage controller connected in parallel with the second cMUT to regulate an amount of transmission signal that passes through the second cMUT.

17. A capacitive micromachined ultrasonic transducer (cMUT) system comprising:
    a first cMUT having a first electrode and a second electrode, the first cMUT being adapted for operation in a transmission mode; and
    a second cMUT having a third electrode and a fourth electrode, the second cMUT being adapted for operation in the reception mode, wherein the first cMUT and the second cMUT are connected to each other to share a common signal line to allow the first cMUT to have a first bias voltage during operation in the transmission mode and the second cMUT to have a second bias voltage during operation in the reception mode, wherein the first electrode is connected to a first bias setter, the second electrode is connected to a second bias setter, different from the first bias setter, the third electrode is connect to a third bias setter, different from the first and second bias setters, and the fourth electrode is connected to a fourth bias setter, different from the first, second and third bias setters.

18. The cMUT system as recited in claim 17, further comprising a voltage controller connected in parallel with the second cMUT to regulate an amount of transmission signal that passes through the second cMUT.

* * * * *